United States Patent [19]
Panzeri et al.

[11] Patent Number: 6,114,345
[45] Date of Patent: Sep. 5, 2000

[54] PHENYLSUBSTITUTED 4-AZASTEROID FLURODERIVATIVES

[75] Inventors: Achille Panzeri, Merate; Marcella Nesi; Enrico Di Salle, both of Milan, all of Italy

[73] Assignee: Pharmacia & Upjohn, S.p.A., Milan, Italy

[21] Appl. No.: 09/300,454

[22] Filed: Apr. 28, 1999

Related U.S. Application Data

[63] Continuation of application No. 08/836,052, filed as application No. PCT/EP96/03518, Aug. 9, 1996, Pat. No. 5,922,728.

[30] Foreign Application Priority Data

Sep. 14, 1995 [GB] United Kingdom .................. 9518858

[51] Int. Cl.$^7$ ................................................ A61K 31/58
[52] U.S. Cl. ................................................ 514/284
[58] Field of Search .................................... 514/284

[56] References Cited

U.S. PATENT DOCUMENTS

| | | | |
|---|---|---|---|
| 5,155,107 | 10/1992 | Panzeri et al. | 514/232.8 |
| 5,407,939 | 4/1995 | Panzeri et al. | 514/284 |
| 5,418,238 | 5/1995 | Panzeri et al. | 514/284 |

FOREIGN PATENT DOCUMENTS 9740062 10/1997 WIPO.

OTHER PUBLICATIONS

George, "Androgen Metabolism in the Prostate of the Finasteride–Treated, Adult Rat," Endocrinology, vol. 138, No. 3, pp. 871–877, Mar. 1997.

Gormley et al., "The Effect of Finasteride in Men with Benign Prostatic Hyperplasia," The New England Journal of Medicine, vol. 327, No. 17, pp. 1185–1191, Oct. 1992.

Panzeri et al "Novel Aromatase and 5alpha–Reductase Inhibitors," J. Steroid Biochem. Molecular Biol., vol. 49, No. 4–6, pp. 289–294, 1994.

Giudici et al., "ECE 28260, a New 5–alpha–Reductase Inhibitor: In Vitro and In Vivo Effects," J. Steroid Biochem. Molec. Biol., vol. 58, No. 3, pp. 299–305, 1996.

di Salle et al., "PNU 157706, a Novel Dual type 1 and II 5–alpha–reductase inhibitor," J. Steroid Biochem. Miolec., vol. 64, No. 3–4, pp. 179–186, 1998.

*Primary Examiner*—Richard L. Raymond
*Attorney, Agent, or Firm*—Oblon, Spivak, McClelland, Maier & Neustadt, P.C.

[57] ABSTRACT

Compounds of formula (I), wherein: the symbol ---- represents a single or a double bond; R is a hydrogen atom or a $C_1$–$C_4$ alkyl group; $R_f$ and $R'_f$, each independently, are $C_1$–$C_4$ alkyl groups substituted by one or more fluorine atoms; and $R_1$ and $R_2$, each independently, are selected from: a hydrogen atom; a phenyl group; a $C_1$–$C_4$ alkyl group unsubstituted or substituted by one or more fluorine atoms; a halogen atom; a cyano (CN) group; a group $OR_4$, wherein $R_4$ is a hydrogen atom or a $C_1$–$C_4$ alkyl group; a group $SR_5$, wherein $R_5$ is a hydrogen atom or a $C_1$–$C_4$ alkyl group; and a group $COR_6$, wherein $R_6$ is a group $OR_4$ in which $R_4$ is as defined above or a $C_1$–$C_4$ alkyl group unsubstituted or substituted by one or more fluorine atoms. They are useful as testosterone 5a-reductase inhibitors.

5 Claims, No Drawings

PHENYLSUBSTITUTED 4-AZASTEROID FLUORODERIVATIVES

This application is a Continuation of application Ser. No. 08/836,052 Filed on May 13, 1997, now U.S. Pat. No. 5,922,728, which is a 371 of International Application No. PCT/EP96/03518, filed Aug. 9, 1996.

The present invention relates to phenylsubstituted 4-azasteroid fluoroderivatives and to a process for their preparation. Moreover, the present invention relates to pharmaceutical compositions containing said phenylsubstituted 4-azasteroid fluoroderivatives and to their use as inhibitors of androgen action, by means of testosterone 5α-reductase inhibition.

In certain androgen responsive tissues the action of testosterone is mediated primarily through its 5α-reduced metabolite, dihydrotestosterone (DHT) (Bruchowsky N., Wilson J. D.; J. Biol. Chem. 243, 5953, 1968). The conversion of testosterone to dihydrotestosterone is catalyzed by the enzyme 5α-reductase and if 5α-reductase is inhibited, the formation of dihydrotestosterone is reduced and its specific androgenic effect is attenuated or prevented.

The 5α-reductase inhibitors may find medical application for the treatment of hyperandrogenic conditions, e.g. certain prostatic diseases, such as benign prostatic hyperplasia and prostatic cancer, and certain skin-hair conditions, such as acne, seborrhoea, female hirsutism and male pattern baldness (Siiteri P. K., Wilson J. D., J. Clin. Invest. 49, 1737, 1970; Price V. H., Arch. Dermatol. III, 1496, 1975; Sandberg A. A., Urology 17, 34, 1981). Also breast cancer treatment can take advantage from use of 5α-reductase inhibitors as the said tumour is known to be aggravated by presence of androgens. Androst-4-en-3-one-17β-carboxylic acid and its methyl ester (Voigt and Hsia, Endocrinology, 92, 1216 (1973); Canadian Patent No. 970,692) are among the first steroidic compounds described as 5α-reductase inhibitors.

Two 5,10-secosteroids having a 3-keto-4,5-diene system in the expanded ring have been found to be selective inhibitors of rat epididymal 5α-reductase (Robaire et al., J. Steroid Biochem. 8, 307–310 (1977)).

The (20R)-4-diazo-21-hydroxy-20-methyl-5α-pregnan-3-one and its analogs are reported to be enzyme activated inhibitors of testosterone 5α-reductase (Blohm et al., Biochem. Biophys. Res. Comm. 95, 273–80 (1980); U.S. Pat. No. 4,317,817).

Another series of enzyme-directed irreversible inhibitors of 5α-reductase have been prepared by introducing a 6-methylene moiety into substrates such as 3-keto-D$^4$-progestins and androgens (Petrow et al., Steroids 38, 352–53 (1981); U.S. Pat. No. 4,396,615).

More recently, on unsaturated derivatives of 3-carboxy steroids have been reported as non-competitive 5α-reductase inhibitors versus testosterone (Biorg. Chem. 17, 372–376 (1989); Eur. Pat. Appln. No. 0289327; Int. Pat. Appln. WO92/20700; Eur. Pat. Appln. No. 0465123; Eur. Pat. Appln. No. 0528485; Eur. Pat. Appln. No. 0567271).

4-Aza steroids are by far the most studied steroid 5α-reductase inhibitors. These compounds are reported in a very large number of publications and patents. In particular the 17β-acylamides and their metabolites are described in: J. Med. Chem. 27, 1690–1701 (1984); J. Med. Chem. 29, 2298–2315 (1986); Eur. Pat. Appln. No. 0004949; U.S. Pat. No. 4,377,584; Eur. Pat. Appln. No. 0155096; U.S. Pat. No. 4,845,104; Eur. Pat. Appln. No. 200859; Eur. Pat. Appln. No. 0462662; Eur. Pat. Appln. No. 484094; U.S. Pat. No. 4,859,681; Int. Pat. Applns. WO91/12261, WO 94/03474, WO 94/03475, WO 94/034476.

The 17β-alkanoyl derivatives are described in J. Med. Chem. 29, 2298–2315 (1986), Eur. Pat. Appln. No. 314119, Eur. Pat. Appln. No. 367502, U.S. Pat. No. 5,061,803, Eur. Pat. Appln. No. 478066.

In Int. Pat. Appln. WO94/03475 fluorinated 17β-substituted-4-aza-5α-androstan-3-one derivatives are disclosed.

We have now found that new di(fluoroalkyl)phenyl-17β-substituted-4-aza-5α-androstan-3-one derivatives as described hereinunder, which fall within the scope of the general formula of WO94/03475, but which are not specifically disclosed therein, are endowed with valuable pharmacological properties.

The present invention provides compounds of formula (I)

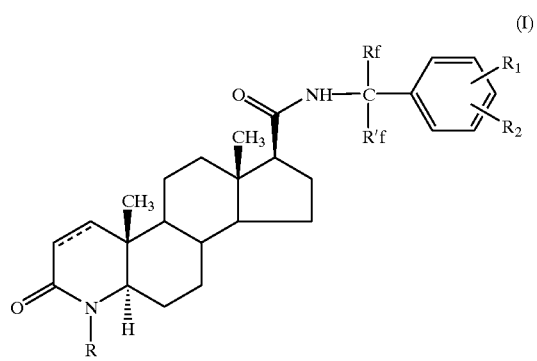

wherein:

the symbol ---- represents a single or a double bond;

R is a hydrogen atom or a $C_1$–$C_4$ alkyl group;

$R_f$ and $R'_f$, each independently, are $C_1$–$C_4$ alkyl groups substituted by one or more fluorine atoms; and $R_1$ and $R_2$, each independently, are selected from:
   a hydrogen atom; a phenyl group; a $C_1$–$C_4$ alkyl group unsubstituted or substituted by one or more fluorine atoms; a halogen atom; a cyano (CN) group; a group $OR_4$, wherein $R_4$ is a hydrogen atom or a $C_1$–$C_4$ alkyl group; a group $SR_5$, wherein $R_5$ is a hydrogen atom or a $C_1$–$C_4$ alkyl group; and a group $COR_6$, wherein $R_6$ is a group $OR_4$ in which $R_4$ is as defined above or a $C_1$–$C_4$ alkyl group unsubstituted or substituted by one or more fluorine atoms.

In the formulae of this specification the dotted line (⋯⋯) indicates a substituent in the α-configuration, i.e. below the plane of the rings, and the wedged line (◀) indicates a substituent in the β-configuration, i.e. above the plane of the rings.

When $R_f$ is different from $R'_f$, the configuration of the chiral centre in the side chain is unspecified; the present invention includes both the single "R" or "S" epimer and the "RS" mixture.

The metabolites and the metabolic precursors of the compounds of formula (I) are within the scope of the present invention.

In the formulae of this specification the alkyl groups may be straight or branched chains. With perfluoroalkyl groups it is meant alkyl groups fully substituted by fluorine atoms.

The $C_1$–$C_4$ alkyl groups may be, for example, methyl, ethyl, n-propyl, iso-propyl, n-butyl, iso-butyl, sec-butyl or tert-butyl.

The $C_1$–$C_4$ alkyl groups substituted by one or more fluorine atoms may be, for example, fluoromethyl, difluoromethyl, trifluoromethyl, 2,2,2-trifluoroethyl, pentafluoroethyl, 3,3,3-trifluoropropyl, 3,3,3,2,2-pentafluoropropyl, heptafluoropropyl, 1,1,1,3,3,3-hexafluoropropyl, nonafluorobutyl or hexafluoroisobutyl.

When R is a $C_1$–$C_4$ alkyl group, it is preferably methyl or ethyl.

The groups $R_f$ and $R'_f$, each independently, preferably contain at least one trifluoromethyl group, and may be selected from trifluoromethyl, 2,2,2-trifluoroethyl, 1,1,1,3,3,3-hexafluoropropyl, and hexafluoroisobutyl, or they may be perfluoro $C_1$–$C_4$ alkyl groups such as, for example, trifluoromethyl, pentafluroethyl, heptafluoropropyl, or nonafluorobutyl.

When $R_1$ is a halogen atom, it may be, for example, chlorine, fluorine, or bromine; preferably, it is fluorine or chlorine.

When $R_1$ is a $C_1$–$C_4$ unsubstituted alkyl group, it is preferably methyl, ethyl, isopropyl, or isobutyl.

When $R_1$ is a $C_1$–$C_4$ alkyl group substituted by one or more fluorine atoms, it is, preferably, trifluoromethyl or pentafluoroethyl.

When $R_1$ is a group —$OR_4$ it is, preferably, methoxy or ethoxy.

When $R_1$ is a group —$SR_5$ it is, preferably, methylthio.

When $R_1$ is a group —$COR_6$, wherein $R_6$ is a group —$OR_4$, it is preferably, —$COOCH_3$, —$COOCH_2CH_3$, or —$COOC(CH_3)_3$.

When $R_1$ is a group —$COR_6$, wherein $R_6$ is a $C_1$–$C_4$ unsubstituted alkyl group, it is preferably, methylcarbonyl, ethylcarbonyl, propylcarbonyl, or butylcarbonyl.

When $R_1$ is a group —$COR_6$, wherein $R_6$ is a $C_1$–$C_4$ alkyl group substituted by one or more fluorine atoms, it is preferably, trifluoromethylcarbonyl, pentafluroethylcarbonyl, heptafluoropropylcarbonyl, or nonafluorobutylcarbonyl.

When $R_2$ is a halogen atom, it may be, for example, chlorine, fluorine or bromine; preferably, it is fluorine or chlorine.

When $R_2$ is a $C_1$–$C_4$ unsubstituted alkyl group, it is, preferably methyl, ethyl, isopropyl, or isobutyl.

When $R_2$ is a $C_1$–$C_4$ alkyl group substituted by one or more fluorine atoms, it is, preferably, trifluoromethyl or pentafluoroethyl.

When $R_2$ is a group —$OR_4$ it is, preferably, methoxy or ethoxy.

When $R_2$ is a group —$SR_5$ it is, preferably, methylthio.

When $R_2$ is a group —$COR_6$, wherein $R_6$ is a group —$OR_4$, it is preferably, —$COOCH_3$, —$COOCH_2CH_3$, or —$COOC(CH_3)_3$.

When $R_2$ is a group —$COR_6$, wherein $R_6$ is a $C_1$–$C_4$ unsubstituted alkyl group, it is preferably, methylcarbonyl, ethylcarbonyl, propylcarbonyl, or butylcarbonyl.

When $R_2$ is a group —$COR_6$, wherein $R_6$ is a $C_1$–$C_4$ alkyl group substituted by one or more fluorine atoms, it is preferably, trifluoromethylcarbonyl, pentafluroethylcarbonyl, heptafluoropropylcarbonyl, or nonafluorobutylcarbonyl.

When one of $R_1$ and $R_2$ is hydrogen and the other is as defined above, the position on the aromatic ring may be orto, meta or para with respect to the position of the 4-azasteroid —CONH— group.

Preferably, when one of $R_1$ and $R_2$ is hydrogen, the other is selected from: hydrogen, p-fluoro, m-fluoro, p-chloro, m-chloro, p-methyl, m-methyl, o-methyl, p-ethyl, m-ethyl, o-ethyl, o-hydroxy, m-hydroxy, p-hydroxy, p-methoxy, m-methoxy, o-methoxy, p-ethoxy, m-ethoxy, o-ethoxy, o-SH, m-SH, p-SH, o-$SCH_3$, m-$SCH_3$, p-$SCH_3$, p-trifluoromethyl, m-trifluoromethyl, o-trifluoromethyl, o-trifluoroacetyl, p-trifluoroacetyl.

When both $R_1$ and $R_2$ are different from hydrogen, the group

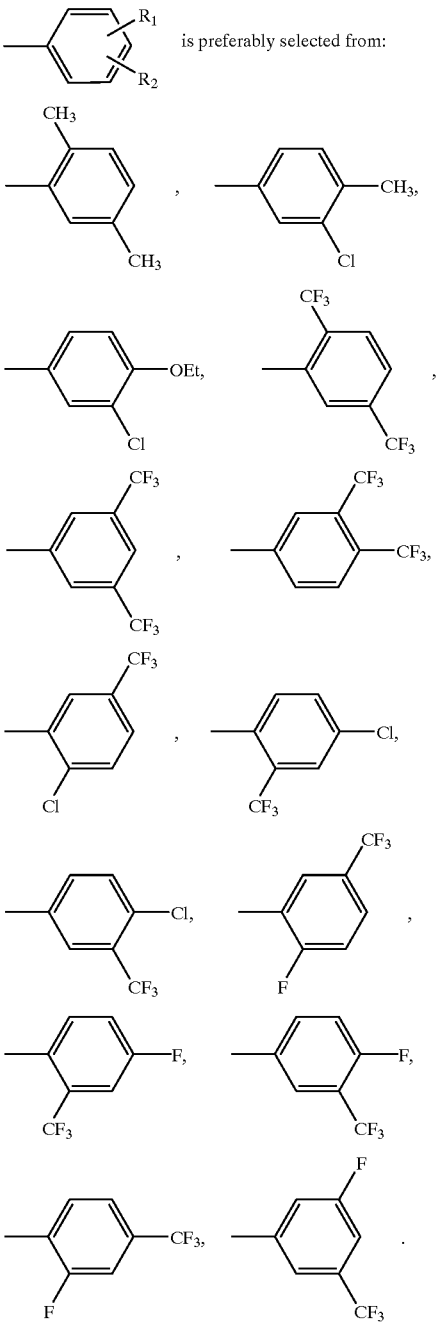

Preferred compounds are those wherein:
the symbol --- is a single or a double bond;
R is hydrogen or methyl;
$R_f$ and $R'_f$ are perfluoroalkyl groups;
$R_1$ is hydrogen, p-fluoro, m-fluoro, o-fluoro, p-chloro, m-chloro, o-chloro, p-methyl, m-methyl, o-methyl, p-trifluoromethyl, m-trifluoromethyl, o-trifluoromethyl, o-methoxy, p-methoxy, or p-trifluoroacetyl;
$R_2$ is hydrogen.

Most preferred compounds are those wherein:
the symbol --- is a single or a double bond;

R is hydrogen or methyl;

$R_f$ and $R'_f$ are trifluoromethyl groups;

$R_1$ is hydrogen, p-fluoro, p-chloro, p-methyl, or p-trifluoromethyl;

$R_2$ is hydrogen.

Specific examples of preferred compounds, according to the invention, are the compounds of formula (I), selected from the group consisting of:

1) N-(1,1,1,3,3,3-hexafluorophenylpropyl)-3-oxo-4-aza-5α-androst-1-ene-17β-carboxamide;
2) N-(1,1,1,3,3,3-hexafluorophenylpropyl)-3-oxo-4-aza-5α-androstane-17β-carboxamide;
3) N-(1,1,1,3,3,3-hexafluorophenylpropyl)-4-methyl-3-oxo-4-aza-5α-androst-1-ene-17β-carboxamide;
4) N-(1,1,1,3,3,3-hexafluorophenylpropyl)-4-methyl-3-oxo-4-aza-5α-androstane-17β-carboxamide;
5) N-[1,1,1,3,3,3-hexafluoro-(4'-methylphenyl)propyl]-3-oxo-4-aza-5α-androst-1-ene-17β-carboxamide;
6) N-[1,1,1,3,3,3-hexafluoro-(4'-fluorophenyl)propyl]-3-oxo- 4-aza-5α-androst-1-ene-17β-carboxamide;
7) N-[1,1,1,3,3,3-hexafluoro-(4'-chlorophenyl)propyl]-3-oxo-4-aza-5α-androst-1-ene-17β-carboxamide;
8) N-[1,1,1,3,3,3-hexafluoro-(4'-trifluoromethylphenyl)propyl]-3-oxo-4-aza-5α-androst-1-ene-17β-carboxamide;
9) N-[1,1,1,3,3,3-hexafluoro-(2',4'-dimethylphenyl)propyl]-3-oxo-4-aza-5α-androst-1-ene-17β-carboxamide;
10) N-[1,1,1,3,3,3-hexafluoro-(4'-phenylphenyl)propyl]-3-oxo-4-aza-5α-androst-1-ene-17β-carboxamide; and
11) N-[1,1,1,3,3,3-hexafluoro-(4'-cyanophenyl)propyl]-3-oxo-4-aza-5α-androst-1-ene-17β-carboxamide.

The above reported preferred compounds are tabulated hereinbelow, with reference to the substituents as defined for formula (I).

TABLE 1

| Cpd | --- | R | $R_f$ | $R'_f$ | $R_1$ | $R_2$ |
| --- | --- | --- | --- | --- | --- | --- |
| 1 | double | H | $CF_3$ | $CF_3$ | H | H |
| 2 | single | H | $CF_3$ | $CF_3$ | H | H |
| 3 | double | $CH_3$ | $CF_3$ | $CF_3$ | H | H |
| 4 | single | $CH_3$ | $CF_3$ | $CF_3$ | H | H |
| 5 | double | H | $CF_3$ | $CF_3$ | p-$CH_3$ | H |
| 6 | double | H | $CF_3$ | $CF_3$ | p-F | H |
| 7 | double | H | $CF_3$ | $CF_3$ | p-Cl | H |
| 8 | double | H | $CF_3$ | $CF_3$ | p-$CF_3$ | H |
| 9 | double | H | $CF_3$ | $CF_3$ | p-$CH_3$ | o-$CH_3$ |
| 10 | double | H | $CF_3$ | $CF_3$ | p-$C_6H_5$ | H |
| 11 | double | H | $CF_3$ | $CF_3$ | p-CN | H |

A compound of formula (I) may be obtained by:
a) reacting a compound of formula (II)

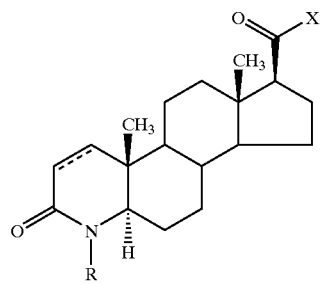

(II)

wherein the symbol ---, and R are as defined above, and X is OH or an activating group of the carboxy function, with a compound of formula (III)

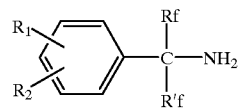

(III)

wherein $R_f$, $R'_f$, $R_1$ and $R_2$ are as defined above, thus obtaining a compound of formula (I); or
b) reducing a compound of formula (IV)

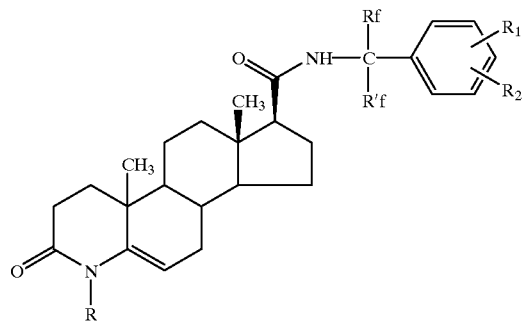

(IV)

wherein R, $R_f$, $R'_f$, $R_1$, and $R_2$ are as defined above, thus obtaining a compound of formula (I), wherein the symbol --- is a single bond, and R, $R_f$, $R'_f$, $R_1$, and $R_2$ are as defined above, and, if desired, dehydrogenating the resulting compound of formula (I) to obtain another compound of formula (I) wherein the symbol --- is a double bond, and R, $R_f$, $R'_f$, $R_1$, and $R_2$ are as defined above, and, if desired, alkylating a compound of formula (I) wherein the symbol --- is a single or double bond, R is an hydrogen atom, $R_1$, $R_2$, $R_f$ and $R'_f$ are as defined above, so obtaining a compound of formula (I) wherein the symbol --- is a single or double bond, R is a $C_1$–$C_4$ alkyl group, $R_1$, $R_2$, $R_f$ and $R'_f$ are as defined above, and, if desired, hydrogenating a compound of formula (I) wherein the symbol --- is a double bond, R is a $C_1$–$C_4$ alkyl group, $R_1$, $R_2$, $R_f$, and $R'_f$ are as defined above to obtain a compound of formula (I) wherein the symbol --- is a single bond, R is a $C_1$–$C_4$ alkyl group, $R_1$, $R_2$, $R_f$ and $R'_f$ are as defined above.

When X is an activating group in the compound of formula (II), it may be any suitable activating group of the carboxy function which is useful in the formation of amidic and peptidic linkages. It may be, for instance, one of the following groups:

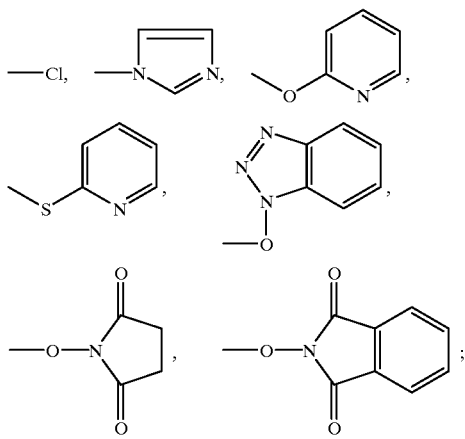

A preferred meaning for X is —Cl.

The reaction of a compound of formula (II) with a compound of formula (III), according to the process variant a) may be carried out in an inert anhydrous solvent such as, for example, methylene chloride, chloroform, dimethylformamide, tetrahydrofurane, acetonitrile, benzene, toluene at a temperature ranging from about room temperature to the refluxing temperature of the reaction mixture, optionally in the presence of an organic base such as, for example, pyridine, p-dimethylamino-pyridine, triethylamine, for a time varying from about one hour to about 48 hours, preferably under an inert atmosphere of nitrogen.

The compounds of formula (III) may be used in the form of N-salt derivatives, preferably hydrochlorides, hydrobromides or trifluoroacetates; in this case the free amino group is formed in situ by means of an organic base such as, for example, a trialkylamine (e.g. triethylamine) or a heterocyclic amine (e.g. pyridine).

The reduction of a compound of formula (IV) as defined above to afford a compound of formula (I), wherein the symbol --- is a single bond, R, $R_1$, $R_2$, $R_f$ and $R'_f$ are as defined above, according to the process b), may be carried out by catalytic hydrogenation.

The reaction can be carried out in an organic solvent such as, for example, ethylacetate, ethanol, methanol, acetic acid, or a mixture thereof, in the presence of a hydrogenation catalyst, such as, for example, platinum oxide (Adams' catalyst), 5% or 10% palladium on charcoal, or palladium hydroxide, under a hydrogen pressure varying from 1 to 10 atm., at a temperature ranging from room temperature to about 70° C. The reduction time typically varies from about 30 minutes to about 5 hours.

The dehydrogenation of a compound of formula (I), wherein the symbol --- is a single bond, R is hydrogen, $R_1$, $R_2$, $R_f$ and $R'_f$ are as defined above, to obtain a compound of formula (I), wherein the symbol --- is a double bond, R is hydrogen, $R_1$, $R_2$, $R_f$ and $R'_f$ are as defined above, may be carried out with benzeneseleninic anhydride (as described in J.Org.Chem. 46, 1442–1446, 1981) or with 2,3-dichloro-5,6-dicyano-1,4-benzoquinone (DDQ) and bis(trimethylsilyl)trifluoroacetamide (BSTFA) (as described in J.Am.Chem. Soc. 110 (10), 3318–3319, 1988) or with iodotrimethylsilane (TMSI), N,N,N',N'-tetramethylethylenediamine (TMEDA) and potassium tert-butylate (as described in J.Org.Chem. 58, 3384–3386, 1993).

The dehydrogenation of a compound of formula (I), wherein the symbol --- is a single bond, R is a $C_1$–$C_4$ alkyl group, $R_1$, $R_2$, $R_f$ and $R'_f$ are as defined above, to obtain a compound of formula (I), wherein the symbol --- is a double bond, R is a $C_1$–$C_4$ alkyl group, $R_1$, $R_2$, $R_f$ and $R'^f$ are as defined above, may be obtained by pyrolysis of 2-phenylsulfinyl derivatives (as described in J.Med.Chem. 29(11), 2298–2315, 1986).

The alkylation of a compound of formula (I), wherein the symbol --- is a single or double bond, R is hydrogen, $R_1$, $R_2$, $R_f$ and $R'_f$ are as defined above, to obtain a compound of formula (I), wherein the symbol --- is a single or double bond, R is a $C_1$–$C_4$ alkyl group, $R_1$, $R_2$, $R_f$ and $R'_f$ are as defined above, can be carried out in an inert solvent such as, for example, dimethylformamide, tetrahydrofurane, diethylether, dimethylsulfoxide, with a strong organic base such as, for example, an alkyllitium derivative, preferably n-butyllitium or tert-butyllitium, or an alkali metal alkoxyde, preferably potassium tert-butylate, or an alkali metal hydride, preferably potassium or sodium hydride, and a $C_1$–$C_4$ alkyl halide, such as, for example, a $C_1$–$C_4$ alkylchloride or a $C_1$–$C_4$ alkylbromide or a $C_1$–$C_4$ alkyliodide, preferably a $C_1$–$C_4$ alkyliodide, at a temperature ranging from about room temperature to reflux temperature of the reaction mixture, for a time varying from about 30 minutes to about 5 hours, preferably under an inert atmosphere of nitrogen or argon.

The hydrogenation of a compound of formula (I), wherein the symbol --- is a double bond, R, $R_1$, $R_2$, $R_f$ and $R'_f$ are as defined above, to obtain a compound of formula (I), wherein the symbol --- is a single bond, R, $R_1$, $R_2$, $R_f$ and $R'_f$ are as defined above, can be performed in a solvent such as, for example, ethylacetate, ethanol, methanol or a mixture of any of these, in the presence of a hydrogenation catalyst, such as, for example, 5% or 10% palladium on charcoal under a hydrogen pressure of about from 1 to 3 atm., for a time ranging from about half an hour to about 3 hours, at room temperature.

A compound of formula (II), wherein the group X is an activating group of the carboxy function, may be obtained from a compound of formula (II), wherein X is an —OH group, by methods well known in the art.

Preferred compounds of formula (II), wherein X is different from OH, are those wherein X is a chlorine atom (acylchlorides). They are obtained treating a compound of formula (II) wherein X is an OH group with freshly distilled chlorinating agent such as, for example, oxalylchloride, or, preferably, thionylchloride ($SOCl_2$), in a solvent such as, for example, tetrahydrofurane, toluene or, preferably, ethanol-free chloroform, optionally in the presence of an organic base such as pyridine, at a temperature ranging from about 0° C. to about 30° C., for about one or two hours, optionally under an inert atmosphere of nitrogen.

The compounds of formula (II), wherein X is an OH group are known compounds (see, for example, J.Med. Chem. 29(11), 2298–2315, 1986).

The amines of formula (III)

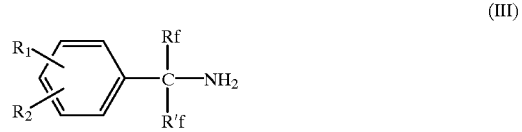

are generally known compounds (see, for example, J.O.C. 30, 1398–1402 (1965) and J.O.C. 33, 1002–1008 (1968)). The compounds of formula (III) may be obtained as described in the papers cited hereabove, or also according to the following scheme:

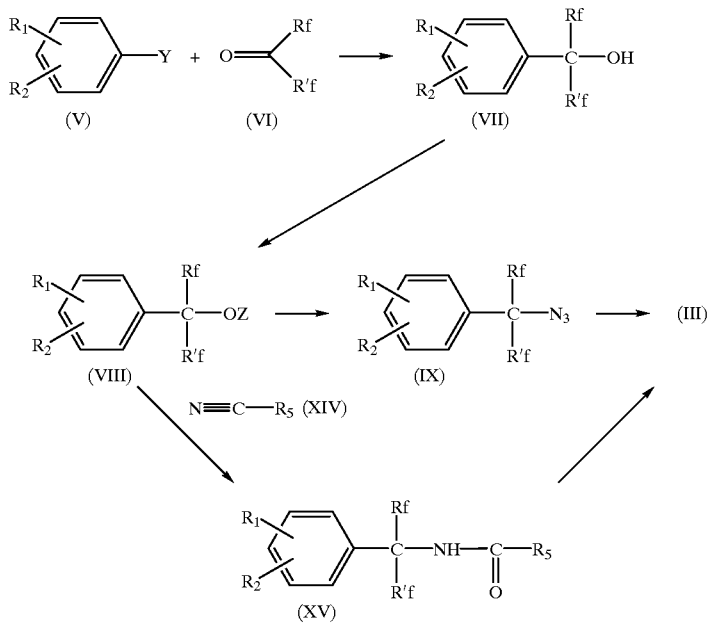

The first reaction step, namely the reaction of (V) with (VI), can be carried out according to known methods (see, for example, J.Am.Chem.Soc. 108, 3470–74, 1986). Some of the compounds of formula (VII) are also commercially available.

The next reaction step converts a compound of formula (VII) into a compound of formula (VIII), wherein —OZ is a leaving group.

Particularly good leaving groups —OZ are those wherein Z is: p-toluensulphonyl (pCH$_3$—Ph—SO$_2$—, abbreviated as Ts), methanesulphonyl (CH$_3$SO$_2$—, abbreviated as Ms), and trifluoromethanesulphonyl (CF$_3$SO$_2$—, abbreviated as Tf).

The conversion of (VII) into (VIII) is advantageously carried out in two steps:

firstly, the alcohol of formula (VII) is treated with a strong base, for example an alkyl lithium, preferably methyl lithium, n-butyl lithium or t-butyl lithium, or an alkali metal hydride such as sodium hydride or potassium hydride, or with an alkali metal alcoholate of a C$_1$–C$_4$ alkyl alcohol such as, for example, sodium or potassium methylate, sodium or potassium ethylate, sodium or potassium tert-butylate, or with an alkali metal bis(trialkylsilyl)amide such as, for example, lithium or sodium or potassium bis(trimethylsilyl)amide, in a suitable solvent, for instance n-hexane, diethylether or tetrahydrofurane, at a temperature ranging from about –30° C. to about 0° C., to yield the corresponding alcoholate. Then such alcoholate is treated with a suitable reagent to give the desired —OZ derivative.

For example, to obtain the above mentioned —OZ groups, the alcoholate can be treated respectively with p-toluensulphonyl chloride (pCH$_3$—Ph—SO$_2$Cl, abbreviated as TsCl), methylsulphonyl chloride (CH$_3$SO$_2$Cl, abbreviated as MsCl) or methanesulphonic anhydride ((CH$_3$SO$_2$)$_2$O, abbreviated as MS$_2$O), and trifluoromethane-sulphonic anhydride ((CF$_3$SO$_2$)$_2$O, abbreviated as Tf$_2$O), optionally in the presence of an organic base, such as a trialkylamine, preferably triethylamine, or pyridine. The reaction is usually carried out at a temperature of from about –30° C. to about room temperature, for a time varying from 30 minutes to two hours.

A particularly preferred —OZ group is —OSO$_2$—CF$_3$ (abbreviated as —OTf), that can be prepared starting from potassium alcoholate as obtained treating the corresponding alcohol of formula (VII) with potassium hydride.

The next reaction step, wherein a compound of formula (VIII) is converted to afford a compound of formula (IX), wherein N$_3$ is an azido group, can be carried out in a solvent such as, for example, dimethylsulphoxide, dimethylfarmamide, ethanol, trifluoroethanol, acetic acid, or trifluoroacetic acid, with an alkali metal azide, such as sodium azide or potassium azide, at a temperature ranging from about 0° C. to about the refluxing temperature of the reaction mixture, for a time varying from about one hour to about 24 hours.

Preferably, sodium azide in trifluoroacetic acid is employed.

The reduction of an azido compound of formula (IX) to an amino compound of formula (III) can be carried out according to well known methods.

Preferably, the reaction is carried out with a Nickel-Raney catalyst using an alcohol as solvent such as, for example, ethanol or, preferably, isopropanol, at about room temperature for a time varying from 15 minutes to about 2 hours. Then the amine (III) is isolated preferably as hydrochloride or hydrobromide, by treatment with gaseous hydrochloric or hydrobromic acid.

Alternatively, the compound of formula (VIII) may be reacted with a nitrile of formula (XIV), wherein R$_5$ is a C$_1$–C$_4$ alkyl group or a phenyl group, to afford an amide of formula (XV) that then is hydrolyzed to the amine of formula (III).

The reaction may be carried out by mixing the compound of formula (VIII) with a nitrile of formula (XIV) in a polar solvent such as, for example, trifluoroacetic acid, 2,2,2-trifluoroethanol, nitromethane, or the nitrile itself in excess, in the presence of a strong inorganic acid such as, for example, fluorosulfonic acid, sulfuric acid or a strong organic acid such as, for example, methanesulfonic acid, trifluoromethanesulphonic acid, trifluoroacetic acid, or a Lewis acid such as, for example, boron trifluoride diethyl etherate (BF$_3$ Et$_2$O), and then by heating the mixture to a temperature of from about 40° C. to about 80° C., for a time varying from about half an hour to about 5 hours, preferably under an inert atmosphere of nitrogen or argon.

Preferred Z group for this transformation is the trifluoromethanesulfonyl group (CF$_3$SO$_2$—, abbreviated as Tf (trifyl)).

The hydrolysis of the amide of formula (XV) to afford the amine of formula (III) may be carried out by treating a suspension of the amide of formula (XV) in water with a strong inorganic acid such as, for example, 98% sulfuric acid or 48% hydrobromic acid, and then by heating the resulting mixture to a temperature varying from about room temperature to about the reflux temperature of the reaction mixture for a time ranging from about 1 hour to about 8 hours, optionally under an inert atmosphere of nitrogen or argon.

A compound of formula (IV), wherein R, R$_1$, R$_2$, R$_f$ and R'$_f$ are as defined above, may be obtained by cyclization of a compound of formula (X)

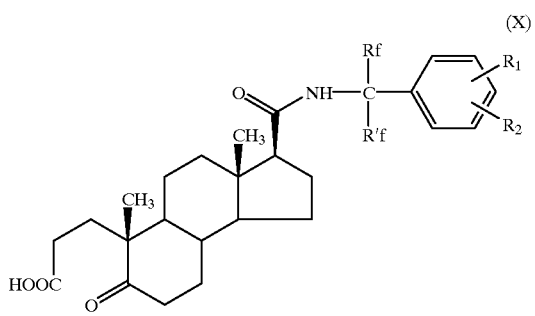

(X)

wherein R$_1$, R$_2$, R$_f$ and R'$_f$ are as defined above, with a compound of formula (XI)

R—NH$_2$ (XI)

wherein R is as defined above, to obtain a compound of formula (IV) as defined above.

The reaction is carried out in a protic or aprotic solvent such as, for example, ethylene glycol, dimethylformamide, dimethylsulphoxide, ethanol, methanol, dioxane, ethylacetate, or a mixture thereof, at a temperature from about 60° C. to about the reflux temperature of the reaction mixture, for a time of from about 30 minutes to about 4 hours. The reaction can be carried out at atmospheric pressure, or also at superatmospheric pressure in an autoclave.

A compound of formula (X) as defined above may be directly obtained by oxidizing a compound of formula (XII)

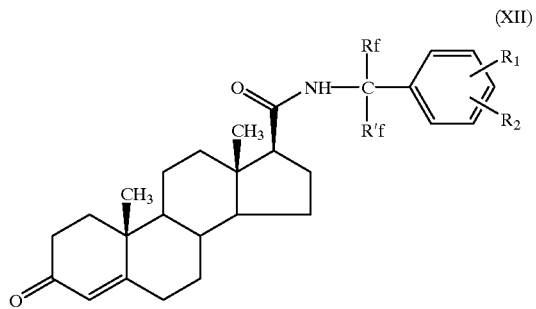

(XII)

wherein R$_1$, R$_2$, R$_f$ and R'$_f$ are as defined above.

The oxidation may be carried out, for example, with an aqueous oxidizing agent, such as sodium metaperiodate, potassium permanganate or ruthenium tetraoxide, under basic conditions, e.g. in the presence of sodium or potassium carbonate, in an organic solvent. The organic solvent can be selected e.g. from C$_1$–C$_5$ alkyl alcohols, such as, t-butanol, isopropanol, ethanol, methanol, and tetrahydrofurane, dioxane, acetone, methylene chloride, or mixtures thereof, at a temperature varying from room temperature to about 60° C., for a reaction time ranging from about one hour to about 5 hours.

Alternatively, the oxidation of the compound of formula (XII) may be carried out with ozone in an organic solvent such as, for example, methanol, ethanol, methylene chloride, ethyl acetate, acetic acid, or a mixture thereof.

Typically the reaction is continued until all the starting material is consumed, and a slight excess of ozone is present (slight blue coloration). The temperature of the reaction is suitably from about −78° C. to room temperature. Eventually, an oxidizing agent is added to the reaction mixture to destroy the resulting ozonide.

A compound of formula (XII) as defined above may be obtained by reacting a compound of formula (XIII)

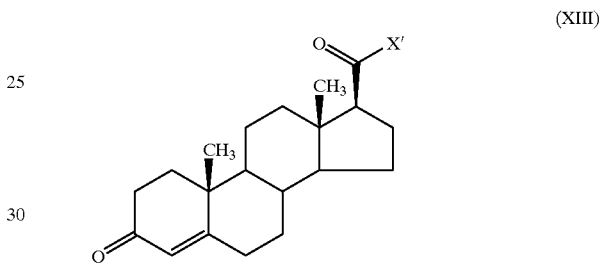

(XIII)

wherein X' is —OH or an activating group of the carboxy function, with a compound of formula (III) as defined above, so obtaining the desired compound of formula (XII).

When X' is an activating group, it can be selected from those mentioned for group X of formula (II).

Analogously to the reaction of (II) with (III), the reaction of a compound of formula (XIII) with a compound of formula (III) may be carried out in an inert anhydrous solvent such as, for example, methylene chloride, chloroform, dimethylformamide, tetrahydrofurane, benzene, toluene, acetonitrile, at a temperature ranging from about room temperature to the refluxing temperature of the reaction mixture, optionally in the presence of an organic base such as, for example, pyridine, p-dimethylaminopyridine, triethylamine, for a time varying from about one hour to about 48 hours, preferably under an inert atmosphere of nitrogen.

The preparation of the compounds of formula (XIII), wherein X' is different from —OH, can be carried out according to the same methods as reported for the compounds of formula (II), starting from the corresponding compounds of formula (XIII) wherein X' is an —OH group, which are known compounds.

The compounds of formula (I) of the present invention inhibit specifically the testosterone 5α-reductase enzyme and, therefore, are potent antiandrogens. For example, the inhibitory effect of the compounds of the invention on 5α-reductase was determined in vitro according to the procedure reported herebelow.

In-Vitro Assay of 5α-Reductase Inhibition

Inhibition of 5α-reductase was evaluated using the particulate fraction from homogenates of hyperplastic human prostates as the enzyme source. The particulate fraction was prepared centrifuging prostate homogenate at 140,000×g.

The resulting pellet, washed several times, was resuspended in buffer and stored at −80° C. in aliquots containing about 10 mg protein/ml.

The assay for 5α-reductase was done in a final volume of 0.5 ml, in 40 mM TRIS-HCl buffer pH 5.5, containing 1 mM dithiothreitol, 5 mM NADPH, 1 μM [$^{14}$C]testosterone, an aliquot of the enzyme preparation and various concentrations of the inhibitors. After 30 min incubation at 37° C. the reaction was terminated by addition of 2 ml cold diethyl ether and the organic phase was separated, evaporated under $N_2$ and resuspended in ethyl acetate.

Testosterone metabolites in this extract were separated in TLC on silica gel F 254 plates (Merck), using chloroform, acetone and n-hexane (2:1:2) as developing solvent system.

Radioactivity on the plate was scanned and analyzed from quantitative plots printed by a TLC-analyzer (Berthold). The fractional 5α-reduction of testosterone was calculated by relating the $^{14}$C-radioactivity in the 5α-reduced metabolites (5α-dihydrotestosterone, 3α- and 3β-androstanediols) regions to the total radioactivity in the testosterone and 5α-reduced metabolites regions.

The concentration of each compound required to reduce control 5α-reductase activity by 50% ($IC_{50}$) was determined by plotting % inhibition versus log for inhibitor concentration.

In-Vivo Inhibition of 5α-Reductase

The standard test for the antiandrogenic effect in rats was used. Prepuberal 22-day-old male rats were castrated via scrotal incision under light ether anaesthesia. On the seventh day after orchiectomy, androgen replacement was performed via subcutaneous implantation of 1 cm-long Silastic$^R$ tube (Dow-Corning, Model No 602-265) filled with a mixture of 25% testosterone and 75% cholesterol. The rats were then treated orally with the tested compounds (7 animals/group), once daily for 7 consecutive days. 24 hours after the last dose the rats were sacrificed and the ventral prostate was removed and weighed. Control animals (testosterone controls) received the vehicle (0.5 ml/kg of 0.5% Methocel/ 0.4% Tween 80). One group of castrated rats was not implanted with testosterone (castrated controls).

The mean percentage of inhibition of the T-induced hypertrophic response of the prostate was calculated according to the following formula:

$$\% \text{ inhibition} = 100 \times (W_{TC} - W_I)/(W_{TC} - W_{CC})$$

where $W_{TC}$, $W_{CC}$ and $W_I$ are the mean prostate weight of testosterone control, castrated control and inhibitor treated group, respectively.

Thus, for example, by using the above described in-vitro assay the compound N-(1,1,1,3,3,3-hexafluorophenylpropyl)-3-oxo-4-aza-5α-androst-1-ene-17β-carboxamide (compound 1) of this invention), was found to cause a very potent inhibition of human 5α-reductase, showing an $IC_{50}$ of 28 nM.

In view of the activity shown in the above test the compounds of the invention can be therapeutically useful in the situations in which a decrease in androgen action, by means of 5α-reductase inhibition, is desirable such as, for example, for the treatment and/or chemoprevention of benign prostatic hyperplasia and of prostatic cancer. Moreover, the compounds of the present invention can be used in the treatment of breast cancer and also of policistic ovary disease as well as of certain skin-hair conditions such as, e.g., acne, seborrhoea, female hirsutism and male pattern baldness. A mammal, e.g., a human or animal, may thus be treated by a method which comprises administering thereto a pharmaceutically effective amount of a compound of formula (I) as defined above.

In the treatment of prostatic cancer, the compound can be administered alone, or combined with other androgen withdrawal modalities such as, e.g., any type of LH-RH agonist or antagonist, or any type of androgen receptor antagonist.

The toxicity of the compounds of the invention is quite negligible, so that they can be safely used in therapy. The compounds of the invention can be administered in a variety of dosage forms, e.g., orally, in the form of tablets, capsules, sugar- or film-coated tablets, liquid solutions or suspensions; rectally, in the form of suppositories; parenterally, e.g., intra-muscularly, or by intravenous injection or infusion; or topically, e.g., in the form of creams.

The dosage depends on the age, weight, conditions of the patient and administration route; for example, the dosage adopted for oral administration to adult humans may range from about 1 to about 200 mg pro dose, from 1 to 3 times daily.

As already said, the invention includes pharmaceutical compositions comprising a compound of the invention in association with a pharmaceutically acceptable excipient (which can be a carrier or diluent).

The pharmaceutical compositions containing the compounds of the invention are usually prepared following conventional methods and are administered in a pharmaceutically suitable form.

For example, the solid oral forms may contain, together with the active compound, diluents, e.g., lactose, dextrose, saccharose, cellulose, corn starch or potato starch; lubricants, e.g., silica, talc, stearic acid, magnesium or calcium stearate, and/or polyethylene glycols; binding agents, e.g., starches, arabic gums, gelatin, methylcellulose, carboxymethylcellulose or polyvinylpyrrolidone; disaggregating agents, e.g., a starch, alginic acid, alginates or sodium starch glycolate; effervescing mixtures; dye-stuffs; sweeteners; wetting agents, such as lecithin, polysorbates, laurylsulphates; and, in general, non-toxic and pharmacologically inactive substances used in pharmaceutical formulations. Said pharmaceutical preparations may be manufactured in known manner, for example, by means of mixing, granulating, tabletting, sugar-coating, or film-coating processes.

The liquid dispersions for oral administration may be, e.g., syrups, emulsions and suspensions. The syrups may contain as carrier, for example, saccharose or saccharose with glycerine and/or mannitol and/or sorbitol; in particular a syrup to be administered to diabetic patients can contain as carriers only products not metabolizable to glucose, or metabolizable in very small amount to glucose, for example, sorbitol.

The suspensions and the emulsions may contain as carrier, for example, a natural gum, agar, sodium alginate, pectin, methylcellulose, carboxymethylcellulose, or polyvinyl alcohol.

The suspensions or solutions for intramuscular injections may contain, together with the active compound, a pharmaceutically acceptable carrier, e.g., sterile water, olive oil, ethyl oleate, glycol, e.g., propylene glycol and if desired, a suitable amount of lidocaine hydrochloride.

The solutions for intravenous injections or infusions may contain as carrier, for example, sterile water or preferably they may be in the form of sterile, aqueous, isotonic saline solutions.

The suppositories may contain together with the active compound a pharmaceutically acceptable carrier, e.g., cocoa-butter, polyethylene glycol, a polyoxyethylene sorbitan fatty acid ester surfactant or lecithin.

Conventional carriers may be used for topical formulations.

The present invention further provides a compound of formula (I) for use in a method of treatment of the human or animal body by therapy, in particular for use as a testosterone 5α-reductase inhibitor or an antiandrogen, for use in the treatment and/or chemoprevention of benign prostatic hyperplasia or of prostatic cancer or for use in the treatment of breast cancer, polycistic ovary disease, acne, seborrhoea, female hirsutism or male pattern baldness.

The present invention further provides the use of a compound of formula (I) in the manufacture of a medicament for use in a method of treatment of breast cancer, polycistic ovary disease, acne, seborrhoea, female hirsutism or male pattern baldness, for use in the treatment and/or chemoprevention of benign prostatic hyperplasia or of prostatic cancer, or for use as an antiandrogen or testosterone 5α-reductase inhibitor.

The following examples further illustrate, but not limit, the invention.

The reported NMR data are determined in deuterochloroform ($CDCl_3$), unless otherwise specified, and are reported as parts per million (δ) downfield from tetramethylsilane.

EXAMPLE 1

(A) 1,1,1,3,3,3-hexafluorophenylpropylamine hydrochloride [Compound (III): $R_1=R_2=H$, $R_f=R'_f=CF_3$, as hydrochloride]

8.34 g of potassium hydride (20% in oil) were washed 3 times with pentane and suspended in diethylether (72 ml). 1,1,1,3,3,3-hexafluorophenylpropanol (9.22 g) was added dropwise over 10 minutes at −10° C. After stirring for 2.25 hours at room temperature, the reaction mixture was cooled again to −10° C. and trifluoroacetic anhydride was added dropwise over 15 minutes. The reaction mixture was stirred for 1 hour at room temperature and then it was quenched with water (50 ml) while maintaining the temperature below +15° C. The organic phase was separated and the aqueous one extracted twice with diethylether (100 ml), dried over sodium sulphate and the solvent removed under vacuum. The crude triflate thus obtained was mixed with sodium azide (4.9 g) and treated at 0° C., dropwise with trifluoroacetic acid (15.2 ml) over 10 minutes. After stirring at room temperature for 6 hours, 32% ammonium hydroxide (100 ml) was added slowly at 0° C. The organic layer was separated and the aqueous one extracted twice with diethylether (100 ml); the combined organic layers were washed throughly with water, dried over sodium sulphate and the solvent removed under vacuum. The crude product was purified by flash chromatography on silica gel (eluant: pentane) to yield 11.34 g of solid 1,1,1,3,3,3-hexafluorophenylpropylazide.

The azido compound was dissolved in isopropanol (125 ml) and treated portionwise with Ni-Raney until the starting material was consumed.

The catalyst was removed by filtration and the isopropanol solution was treated with gaseous hydrochloric acid. After evaporating the solvent, 6.89 g of white solid 1,1,1,3,3,3-hexafluorophenylpropylamine hydrochloride were obtained.

NMR (DMSO) δ: 4.50–5.70 (bs, $NH_3^+$), 7.45–7.80 (m, 5H, Ph); MS (EI) m/z: 243 $M^{+\cdot}$, 174 $M—^{\cdot}CF_3^{1+}$, 104 $M—^{\cdot}CF_3—HCF_3^{1+}$ (B) N-(1,1,1,3,3,3-hexafluorophenylpropyl)-3-oxo-4-aza-5α-androst-1-ene-17β-carboxamide [Compound (I): R=H, $R_f=R'_f=CF_3$, $R_1=R_2=H$, ---=double bond]

A solution of thionyl chloride (15 ml) in chloroform (9 ml) was added dropwise to a suspension of 3-oxo-4-aza-5α-androst-1-ene-17β-carboxylic acid (3 g) in chloroform (50 ml), over about 30 minutes at 0° C. After stirring at room temperature for 1 h, the volatile products were removed under vacuum and the white solid 3-oxo-4-aza-5α-androst-1-ene-17β-carbonyl chloride so obtained was dissolved in chloroform (157 ml), cooled to −3° C. and treated with 1,1,1,3,3,3-hexafluorophenylpropylamine hydrochloride (5.3 g) and pyridine (2.248 ml). The reaction mixture was heated to reflux for 7 hours. After staying overnight at room temperature the reaction mixture was diluted with chloroform, washed with 1N HCl (2×100 ml), with brine, with water until neutral and dried over sodium sulphate. The solvent was evaporated under vacuum and the crude yellow solid purified by flash chromatography on silica gel (eluant: methylene chloride/acetone 85:15) to yield 920 mg of the title compound.

NMR ($CDCl_3$) δ: 7.38–7.54 (m,5H, Ph), 6.79 (d, 1H, H(1)), 5.89 (bs, 1H, NH(21)), 5.82 (dd, 1H, H(2)), 5.39 (bs, 1H, NH(4)), 3.33 (dd, 1H, H(5α)), 0.98 (s, 3H, Me(19)), 0.76 (s, 3H, Me(18)); MS ($FAB^-$) m/z: 541 $M–H^{1-}$, 471 $M–HCF_3–H^{1-}$; Elemental analysis; calculated: C, 61.98; H, 5.94; N, 5.16; found: C, 61.97; H, 6.39; N, 4.69.

EXAMPLES 2–4

Following a procedure analogous to Example 1, part (B), and using the same amine hydrochloride prepared in Example 1, part (A), and the appropriate aza-steroid acid, the following compounds were prepared:

N-(1,1,1,3,3,3-hexafluorophenylpropyl)-3-oxo-4-aza-5α-androstane-17β-carboxamide:

NMR ($CDCl_3$) δ: 7.50–7.30 (m, 5H, Ph), 5.88 (bs, 1H, NH(21)), 5.42 (bs, 1H, NH(4)), 3.08 (dd, 1H, H(5α)), 2.42 (m, 2H, $CH_2(2)$), 0.90 (s, 3H, Me(19), 0.76 (s, 3H, Me(18) (Example 2);

N-(1,1,1,3,3,3-hexafluorophenylpropyl)-4-methyl-3-oxo-4-aza-5α-androst-1-ene-17β-carboxamide:

NMR ($CDCl_3$) δ: 7.38–7.54 (m,5H, Ph), 6.69 (dd, 1H, H(1)), 5.89 (bs, 1H, NH(21)), 5.87 (dd, 1H, H(2)), 3.36 (dd, 1H, H(5α)), 2.95 (s, 3H, $NCH_3$), 0.94 (s, 3H, Me(19)), 0.76 (s, 3H, Me(18)) (Example 3);

N-(1,1,1,3,3,3-hexafluorophenylpropyl)-4-methyl-3-oxo-4-aza-5α-androstane-17β-carboxamide:

NMR ($CDCl_3$) δ: 7.50–7.30 (m,5H, Ph), 5.88 (bs, 1H, NH(21)), 3.05 (dd, 1H, H(5α)), 2.93(s, 3H, $NCH_3$), 2.46 (m, 2H, $CH_2(2)$), 0.90 (s, 3H, Me(19)), 0.76 (s, 3H, Me(18)) (Example 4).

EXAMPLES 5–6

(A) Following a procedure analogous to Example 1, part (A), the following amines hydrochlorides corresponding to formula (III) were prepared:

1,1,1,3,3,3-hexafluoro-(4'-methylphenyl)propylamine hydrochloride [Compound (III): $R_1$=p-$CH_3$, $R_2$=H, $R'_f=R_f=CF_3$, as hydrochloride]

NMR (DMSO) δ: 2.35 (s, 3H, $pCH_3Ph$), 7.29 and 7.58 (2d, 4H, p-substituted Ph); MS (EI) m/z: 257 $M^{+\cdot}$, 188 $M–^{108}CF_3^{1+}$, 118 $M–^{\cdot}CF_3–HCF_3^{1+}$, 91 $C_7H_7$ (Example 5A)

1,1,1,3,3,3-hexafluoro-(4'-trifluoromethylphenyl)propylamine hydrochloride [Compound (III): $R_1$=p-$CF_3$, $R_2$=H, $R'_f=R_f=CF_3$, as hydrochloride] (Example 6A)

(B) Following a procedure analogous to Example 1, part (B), and using the amine hydrochlorides prepared in part (A) above, and the same starting aza-steroidic acid of Example 1, the following compounds corresponding to formula (I) were prepared:

N-[1,1,1,3,3,3-hexafluoro-(4'-methylphenyl)propyl]-3-oxo-4-aza-5α-androst-1-ene-17β-carboxamide [Compound (I): R=H, $R_1$=p-$CH_3$, $R_2$=H, $R_f=R'_f=CF_3$, ---=double bond]

NMR (CDCl$_3$) δ: 0.76 (s, 3H, CH$_3$(18)), 0.98 (s, 3H, CH$_3$(19)), 2.35 (s, 3H, CH$_3$—Ph), 3.33 (dd, 1H, H(5α)), 5.37 (s, 1H, NH(21)), 5.79 (s, 1H, NH(4)), 5.82 (dd, 1H, H(2)), 6.78 (d, 1H, H(1)), 7.19 and 7.36 (2d, 4H, p-substituted Ph) MS (FAB$^-$) m/z: 555 M–H$^{1-}$, 485 M–HCF$_3$–H$^{1-}$; Elemental analysis; calculated: C, 62.58; H, 6.61; N, 5.03; found: C, 62.48; H, 6.66; N, 4.65; (Example 5B).

N-[1,1,1,3,3,3-hexafluoro-(4'-trifluoromethylphenyl)propyl]-3-oxo-4-aza-5α-androst-1-ene-17β-carboxamide [Compound (I): R=H, R$_1$=p-F, R$_2$=H, R$_f$=R'$_f$=CF$_3$, ---=double bond]

NMR (CDCl$_3$) δ: 0.76 (s, 3H, CH$_3$(18)), 0.98 (s, 3H, CH$_3$(19)), 3.33 (dd, 1H, H(5α)), 5.37 (s, 1H, NH (21)), 5.79 (s, 1H, NH(4)), 5.82 (dd, 1H, H(2)), 6.78 (d, 1H, H(1)), 7.18 and 7.54 (2d, 4H, p-substituted Ph); MS (FAB$^-$) m/z: 559 M–H$^{1-}$; 489 M–HCF$_3$–H$^{1-}$; (Example 6B).

EXAMPLE 7

(A) 1,1,1,3,3,3-Hexafluoro-(4'-fluorophenyl)propyl amine [compound (III): R$_1$=p-F, R$_2$=H, R$_f$=R'$_f$=CF$_3$]

A solution of 1,1,1,3,3,3-hexafluoro-(4-fluorophenyl)-propanol (5.243 g) in anhydrous diethylether (15 mL) was added dropwise, over about 15 minutes, to a suspension of potassium tertbutylate (2.469 g) in anhydrous diethylether (15 mL) maintaining the internal temperature between 0° C. and −5° C., under an inert atmosphere of nitrogen. After 10 minutes the pink solution was treated dropwise with neat trifluoromethanesulfonic anhydride (7.236 mL) at 0° C. −5° C., over about 15 minutes. After stirring at room temperature for 4 hours, the reaction mixture was cooled to −10° C. and quenched with water (20 mL). The organic phase was separated, washed with brine (6×20 mL) and dried over sodium sulfate. After evaporation of the solvent the crude was purified by flash chromatography on silica gel (eluant: n-hexane/ethyl acetate 9:1) to afford 4.07 g of 1,1,1,3,3,3-hexafluoro-(4-fluorophenyl)propyl-trifluoromethanesulfonate.

The triflate so obtained (4.07 g) was treated at room temperature, under stirring, with benzonitrile (2.1 mL) and trifluoroacetic acid (2.1 mL) and the mixture was heated to 60° C. for 2.25 hours. After cooling to room temperature the reaction mixture was treated with saturated aqueous sodium carbonate (100 mL) and extracted with diethylether (150 mL). The combined organic extract were washed with saturated aqueous sodium chloride and anhydrified over sodium sulphate. After evaporation of the solvent the crude product was purified by flash chromatography on silica gel (eluant: n-hexane/ethyl acetate 6:4) to yield 763 mg of N-[1,1,1,3,3,3-hexafluoro-(4-fluorophenyl)propyl] benzamide.

The benzamide (0.866 mg) was suspended in a mixture of 98% sulfuric acid/water (10:1, v/v, 11 mL) and heated to reflux (110° C.) for 6 hours. After diluting with water (15 mL), the solution was extracted thoroughly with diethylether (5×20 mL). The organic extracts were washed with 1N aqueous sodium hydrogen carbonate, with saturated aqueous sodium chloride and dried over sodium sulphate. The crude obtained after evaporating the solvent was purified by flash chromatography on silica gel (eluant: n-hexane/ethyl acetate 9:1) to afford 658 mg of the title compound.

(B) N-[1,1,1,3,3,3-hexafluoro-(4'-fluorophenyl)propyl]-3-oxo-4-aza-5α-androst-1-ene-17β-carboxamide [compound (I): R=H, R$_1$=p-F, R$_2$=H, R$_f$=R'$_f$=CF$_3$, ---=double bond]

A solution of thionyl chloride (3.1 mL) in chloroform (5 mL) was added dropwise to a suspension of 3-oxo-4-aza-5α-androst-1-ene-17β-carboxylic acid (635 mg) in chloroform (28 mL), over about 30 minutes at 0° C. After stirring at room temperature for two hours, the volatile compounds were removed under vacuum and the white solid 3-oxo-4-aza-5α-androst-1-ene-17β-carbonyl chloride so obtained was dissolved in chloroform, cooled to −8° C. and treated with pyridine (0.387 mL) and with the 1,1,1,3,3,3-hexafluoro-(4'-fluorophenyl)propyl amine (626 mg) dissolved in chloroform (1 mL). The reaction mixture was heated at reflux for 8 hours and then was left overnight at room temperature. A further amount of pyridine (0.387 mL) was added and then the reaction mixture was refluxed until a clear solution was obtained (8 hours). After cooling to room temperature the solution was washed with 1N hydrochloric acid (20 mL), with saturated aqueous sodium chloride (5×5 mL), with water and dried over sodium sulfate. After evaporating the solvent, the crude solid (1.2 g) was purified by flash chromatography on silica gel (eluant: toluene/ethyl acetate/methanol 75:20:5) to afford 95 mg of the title compound.

NMR (CDCl$_3$) δ: 7.18 and 7.54 (2d, 4H, p-substituted-Ph), 6.78 (d, 1H, H(1)), 5.82(dd, 1H, H(2)), 5.81 (bs, 1H, NH(21)), 5.32 (bs, 1H, NH(4)), 3.33 (dd, 1H, H(5α)), 0.98 (s, 3H, Me(19)), 0.76 (s, 3H, Me(18)); MS(FAB$^-$) m/z: 559 [M–H]$^-$, 489 [M–HCF$_3$–H]$^-$.

EXAMPLE 8

(A) Following a procedure analogous to Example 7, part (A), the following amines of formula (III) were prepared:

1,1,1,3,3,3-hexafluorophenylpropyl amine;

1,1,1,3,3,3-hexafluoro-(4'-methylphenyl)propyl amine;

1,1,1,3,3,3-hexafluoro-(4'-chlorophenyl)propyl amine;

1,1,1,3,3,3-hexafluoro-(4'-trifluoromethylphenyl)propyl amine;

1,1,1,3,3,3-hexafluoro-(2',4'-dimethylphenyl)propyl amine;

1,1,1,3,3,3-hexafluoro-(4'-phenylphenyl)propyl amine; and 1,1,1,3,3,3-hexafluoro-(4'-cyanophenyl)propyl amine.

(B) Following a procedure analogous to Example 7, part (B), using the amines prepared in part (A) and the same starting azasteroidic acid of Example 1, the following compounds of formula (I) were prepared:

N-[1,1,1,3,3,3-hexafluorophenylpropyl]-3-oxo-4-aza-5α-androstane-17β-carboxamide:

NMR (CDCl$_3$) δ: 7.50–7.30 (m,5H, Ph), 5.88 (bs, 1H, NH(21), 5.42 (bs, 1H, NH(4)), 3.08 (dd, 1H, H(5α)), 2.42 (m, 2H, CH$_2$(2)), 0.90 (s, 3H, Me(19)), 0.76 (s, 3H, Me(18));

N-[1,1,1,3,3,3-hexafluorophenylpropyl]-3-oxo-4-aza-5α-androst-1-ene-17β-carboxamide:

NMR (CDCl$_3$) δ: 7.38–7.54 (m,5H, Ph), 6.79 (d, 1H, H(1)), 5.89 (bs, 1H, NH(21)), 5.82 (dd, 1H, H(2)), 5.39 (bs, 1H, NH(4)), 3.33 (dd, 1H, H(5α)) 0.98 (s, 3H, Me(19)), 0.76 (s, 3H, Me(18);

N-[1,1,1,3,3,3-hexafluorophenylpropyl]-4-methyl-3-oxo-4-aza-5α-androstane-17β-carboxamide:

NMR (CDCl$_3$) δ: 7.50–7.30 (m,5H, Ph), 5.88 (bs, 1H, NH(21)), 3.05 (dd, 1H, H(5α)), 2.93(s, 3H, NCH$_3$), 2.46 (m, 2H, CH$_2$(2)), 0.90 (s, 3H, Me(19)), 0.76 (s, 3H, Me(18));

N-[1,1,1,3,3,3-hexafluorophenylpropyl]-4-methyl-3-oxo-4-aza-5α-androst-1-ene-17β-carboxamide:

NMR (CDCl$_3$) δ: 7.38–7.54 (m,5H, Ph), 6.69 (dd, 1H, H(1)), 5.89 (bs, 1H, NH(21)), 5.87 (dd, 1H, H(2)), 3.36 (dd, 1H, H(5α)), 2.95 (s, 3H, NCH$_3$), 0.94 (s, 3H, Me(19)), 0.76 (s, 3H, Me(18));

N-[1,1,1,3,3,3-hexafluoro-(4'-methylphenyl)propyl]-3-oxo-4-aza-5α-androst-1-ene-17β-carboxamide:

NMR (CDCl$_3$) δ: 7.19 and 7.36 (2d, 4H, p-substituted-Ph), 6.78 (d, 1H, H(1)), 5.82 (dd, 1H, H(2)), 5.79 (s, 1H, NH(21)), 5.37 (bs, 1H, NH(4)), 3.33 (dd, 1H, H(5α)), 2.35 (s, 3H, CH$_3$—Ph), 0.98 (s, 3H, Me(19)), 0.76 (s, 3H, Me(18));
N-[1,1,1,3,3,3-hexafluoro-(4'-chlorophenyl)propyl]-3-oxo-4-aza-5α-androst-1-ene-17β-carboxamide:
NMR (CDCl$_3$) δ: 7.31–7.45 (2d, 4H, p-substituted-Ph), 6.78 (d, 1H, H(1)), 5.82(dd, 1H, H(2)), 5.81 (s, 1H, NH(21)) 5.35 (bs, 1H, NH(4)), 3.33 (dd, 1H, H(5α)), 0.98 (s, 3H, Me(19)), 0.73 (s, 3H, Me(18));
N-[1,1,1,3,3,3-hexafluoro-(4'-trifluoromethylphenyl)-propyl]-3-oxo-4-aza-5α-androst-1-ene-17β-carboxamide;
N-[1,1,1,3,3,3-hexafluoro-(2',4'-dimethylphenyl)propyl]-3-oxo-4-aza-5α-androst-1-ene-17β-carboxamide:
NMR (CDCl$_3$) δ: 7.31 and 7.08 (2m, 3H, o,p-substituted-Ph), 6.78 (d, 1H, H(1)), 5.82 (dd, 1H, H(2)), 5.79 (s, 1H, NH(21)), 5.45 (bs, 1H, NH(4)), 3.33 (dd, 1H, H(5α)), 2.35 and 2.32 (2s, 6H, 2',4' (CH$_3$)$_2$Ph), 0.96 (s, 3H, Me(19)), 0.72 (s, 3H, Me(18));
N-[1,1,1,3,3,3-hexafluoro-(4'-phenylphenyl)propyl]-3-oxo-4-aza-5α-androst-1-ene-17β-carboxamide; and
N-[1,1,1,3,3,3-hexafluoro-(4'-cyanophenyl)propyl]-3-oxo-4-aza-5α-androst-1-ene-17β-carboxamide.

EXAMPLE 9

N-[1,1,1,3,3,3-hexafluorophenylpropyl]-3-oxoandrost-4-ene-17β-carboxamide [compound (XII): R$_1$=R$_2$=H, R$_f$=R'$_f$=CF$_3$]

To a stirred solution of 3-oxoandrost-4-ene-17β-carboxylic acid (30 g) in methylene chloride (300 mL) and dimethylformamide (1.82 mL) a solution of oxalyl chloride (9.28 mL) in methylene chloride (30 mL) was added dropwise at 0° C. under nitrogen atmosphere. After stirring at 0° C. for 1 hour the reaction was completed. The volatile compounds were removed under vacuum, the solid was taken up with cyclohexane (200 mL) and evaporated to dryness (twice). The 3-oxo-androst-4-ene-17β-carbonyl chloride (30.33 g) so obtained was dissolved in chloroform (1.5 L), cooled to 0° C. and treated with 1,1,1,3,3,3-hexafluorophenylpropyl amine (46.078 g) and pyridine (38.3 mL). The reaction mixture was heated at reflux for 7 hours. After staying overnight at room temperature the reaction mixture was washed with 1N HCl (2×100 mL), with brine, with water until neutral and dried over sodium sulfate. The solvent was evaporated under vacuum and the brownish solid purified by flash chromatography on silica gel (eluant: n-hexane/ethyl acetate 70/30) to yield 9.2 g of the title compound.

NMR (CDCl$_3$) δ: 0.77 (s, 3H, Me (18)), 1.29 (s, 3H, Me (19)), 5.72 (m, 1H, CH (4)), 5.93 (s, 1H, NH), 7.36–7.55 (m, 5H, Ph).

17β-[N-(1,1,1,3,3,3-hexafluorophenylpropyl)carbamoyl]-5-oxo-4-nor-3,5-secoandrostan-3-oic acid [compound (X): R$_1$=R$_2$=H, R$_f$=R'$_f$=CF$_3$]

To a solution of N-(1,1,1,3,3,3-hexafluorophenylpropyl)-3-oxoandrost-4-ene-17β-carboxamide (1, 70 g; 3.486 mmol) in tert-butanol (40 mL) and 2M aqueous sodium carbonate (2.09 mL), a 2% aqueous potassium permanganate solution (1.8 mL) and a 0.75M aqueous sodium metaperiodate solution (30 mL) were added dropwise simultaneously, over about 5 minutes, at about 40° C., at such a rate that the colour of the reaction mixture remains always pink. After stirring at 40° C. for 1 h and 15 minutes, the reaction mixture was cooled to room temperature, filtered and the tert-butanol was removed from the filtrate by evaporation under vacuum (40 mL of solvent were collected). Then the solution was cooled to about 0° C., diluted with water, acidified with 1N hydrochloric acid and extracted with ethyl acetate (4×30 mL) and with methylene chloride (2×30 mL); the collected organic extracts were washed with water (2×30 mL), brine (20 mL) and anhydrified over sodium sulfate. Evaporation of the solvent left a solid foam, that was purified by flash chromatography (eluant: n-hexane/ethyl acetate 50:50) to yield 1.656 g of solid white compound.

NMR (CDCl$_3$) δ: 7.36–7.54 (m,5H, Ph), 5.84 (s, 1H, NH), 1.14 (s, 3H, Me(19)), 0.78 (s, 3H, Me(18)). MS (FAB$^+$) (m/z): 562 [M+H]$^+$, 544 [M–H$_2$O+H]$^+$, 390 [M–·C(CF$_3$)$_2$Ph+2H]$^+$, 227 Ph(CF$_3$)$_2$C$^+$.

N-(1,1,1,3,3,3-hexafluorophenylpropyl)-3-oxo-4-aza-androst-5-ene-17β-carboxamide [compound (IV): R=R$_1$=R$_2$=H, R$_f$=R'$_f$=CF$_3$]

A suspension of 17β-[N-(1,1,1,3,3,3-hexafluorophenylpropyl) carbamoyl]-5-oxo-4-nor-3,5-secoandrostan-3-oic acid (1.540 g) in anhydrous ethylene glycol (35 mL) was saturated at 0° C. with anhydrous gaseous ammonia: the secoacid dissolved completely. The solution so obtained was heated slowly to 180° C. over 1 hour and 10 minutes and maintained at this temperature for 20 minutes. Then, the temperature was allowed to reach room temperature over 0.5 hour. The yellowish solution was cooled to about 0° C. under good stirring: the final compound began to precipitate. After diluting with water (30 mL) the stirring was continued for 0.5 hour at 0° C. and the precipitate was filtered and washed with water. There were obtained 1.36 g of a pale brownish solid that was purified by flash chromatography on silica gel (eluant: n-hexane/ethyl acetate 50:50) to afford 1.090 g of the title compound.

NMR (CDCl$_3$) δ: 7.60–7.37 (m,5H, Ph), 5.83 (s, 1H, NH), 4.81 (m, 1H, H(6)), 1.11 (s, 3H, Me(19)), 0.76 (s, 3H, Me(18)).

N-(1,1,1-3,3,3-hexafluorophenylpropyl)-3-oxo-4-aza-5α-androstane-17β-carboxamide [compound (I): R=R$_1$=R$_2$=H, R$_f$=R'$_f$=CF$_3$, ---=single bond]

A solution of N-(1,1,1,3,3,3-hexafluorophenylpropyl)-3-oxo-4-aza-androst-5-ene-17β-carboxamide (200 mg) in glacial acetic acid (15 mL) was hydrogenated in the presence of PtO$_2$ (Adams catalyst) (40 mg) under a pressure of 45 psi of hydrogen at 45° C. for 1 h. The reaction mixture was cooled at room temperature, the catalyst was filtered off and the solvent was removed under reduced pressure. The residue was taken up with methylene chloride, washed with 1N sulfuric acid, with brine, with aqueous sodium carbonate, with brine, with water, dried over sodium sulfate and the solvent was removed under vacuum. The crude solid so obtained was purified by flash chromatography on silica gel (eluant: toluene/ethyl acetate/methanol 75:20:5) to yield 150 mg of the title compound.

NMR (CDCl$_3$) δ: 7.50–7.30 (m, 5H, Ph), 5.88 (bs, 1H, NH(21)), 5.42 (bs, 1H, NH(4)), 3.08 (dd, 1H, H(5α)), 2.42 (m, 2H, CH$_2$(2)), 0.90 (s, 3H, Me(19)), 0.76 (s, 3H, Me(18)).

N-(1,1,1,3,3,3-hexafluorophenylpropyl)-3-oxo-4-aza-5α-androst-1-ene-17β-carboxamide [compound (I): R=R$_1$=R$_2$=H, R$_f$=R'$_f$=CF$_3$, ---=double bond]

To a solution of N-(1,1,1,3,3,3-hexafluorophenylpropyl)-3-oxo-4-aza-5α-androstane-17β-carboxamide (106 mg) in chlorobenzene (5 mL) phenylseleninic anhydride (108.3 mg) was added. The solution was refluxed for 5 h, while water was removed by a Marcusson device. The solution was evaporated and the residue was dissolved in methylene chloride, washed with aqueous sodium carbonate, saturated sodium chloride solution, water and dried over sodium sulfate. After evaporating the solvent, the crude was purified by flash chromatography (eluant: toluene/ethyl acetate/methanol 75:20:5) to yield 70 mg of the title compound.

NMR (CDCl$_3$) δ: 7.38–7.54 (m,5H, Ph), 6.79 (d, 1H, H(1)), 5.89 (bs, 1H, NH(21)), 5.82 (dd, 1H, H(2)), 5.39 (bs, 1H, NH(4)), 3.33 (dd, 1H, H(5α)), 0.98 (s, 3H, Me(19)), 0.76 (s, 3H, Me(18)).

EXAMPLE 10

Scored tablets for oral use, each containing 250 mg of the active substance, were manufactured as follows.

Composition (for 10,000 tablets):

| | |
|---|---|
| N-(1,1,1,3,3,3-hexafluorophenylpropyl)-3-oxo-4-aza-5α-androst-1-ene-17β-carboxamide | 2500 g |
| Corn starch | 275 g |
| Talc powder | 187 g |
| Calcium stearate | 38 g |

The active substance was granulated with a 4% w/v aqueous solution of methyl cellulose. To the dried granules a mixture of the remainder of the ingredients was added and the final mixture compressed into tablets of proper weight.

EXAMPLE 11

Two-piece hard gelatin capsules for oral use, each containing 250 mg of active substance were manufactured as follows.

Composition for 10,000 capsules:

| | |
|---|---|
| N-(1,1,1,3,3,3-hexafluorophenylpropyl)-3-oxo-4-aza-5α-androst-1-ene-17β-carboxamide | 2500 g |
| Lactose | 1000 g |
| Corn starch | 300 g |
| Talc powder | 65 g |
| Calcium stearate | 35 g |

The active substance was mixed with the starch-lactose mixture followed by the talc and calcium stearate.

What is claimed is:

1. A method for treating prostatic cancer and chemoprevention of benign prostatic hyperplasia or of prostatic cancer, comprising administering to a patient in need thereof an effective amount of a compound of formula (I):

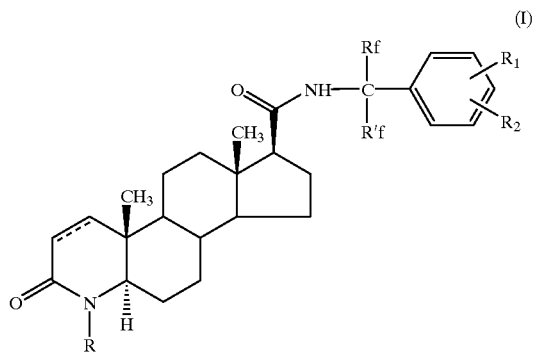

wherein:
the symbol --- represents a single or a double bond;
R is a hydrogen atom or a C$_1$–C$_4$ alkyl group;
R$_f$ and R'$_f$, each independently, are perfluoro C$_1$–C$_4$ alkyl groups;
R$_1$ and R$_2$, each independently, are selected from the group consisting of:
a hydrogen atom; a phenyl group; a C$_1$–C$_4$ alkyl group unsubstituted or substituted by one or more fluorine atoms; a halogen atom; a cyano (CN) group; a group OR$_4$, wherein R$_4$ is a hydrogen atom or a C$_1$–C$_4$ alkyl group; a group SR$_5$, wherein R$_5$ is a hydrogen atom or a C$_1$–C$_4$ alkyl group; and a group COR$_6$, wherein R$_6$ is a group OR$_4$ in which R$_4$ is as defined above or a C$_1$–C$_4$ alkyl group unsubstituted or substituted by one or more fluorine atoms.

2. The method according to claim 1, wherein in said compound of formula (I):

R is hydrogen or methyl;

R$_1$ is hydrogen, p-fluoro, m-fluoro, o-fluoro, p-chloro, m-chloro, o-chloro, p-methyl, m-methyl, o-methyl, p-trifluoromethyl, m-trifluoromethyl, o-tetrafluoromethyl, o-methoxy, p-methoxy, or o-trifluoroacetyl; and R$_2$ is hydrogen.

3. The method according to claim 1, wherein in said compound of formula (I):

R is hydrogen or methyl

R$_f$ and R'$_f$ are trifluoromethyl groups;

R$_1$ is hydrogen, p-fluoro, p-chloro, p-methyl, or p-trifluoromethyl; and

R$_2$ is hydrogen.

4. The method according to claim 1, wherein said compound (I) is selected from the group consisting of:

N-(1,1,1,3,3,3-hexafluorophenylpropyl)-3-oxo-4-aza-5α-androst-1-ene-17β-carboxamide;

N-(1,1,1,3,3,3-hexafluorophenylpropyl)-3-oxo-4-aza-5α-androstane-17β-carboxamide;

N-(1,1,1,3,3,3-hexafluorophenylpropyl)-4-methyl-3-oxo-4-aza-5α-androst-1-ene-17β-carboxamide;

N-(1,1,1,3,3,3-hexafluorophenylpropyl)-4-methyl-3-oxo-4-aza-5α-androstane-17β-carboxamide;

N-(1,1,1,3,3,3-hexafluoro-(4'-methylphenyl)propyl]-3-oxo-4-aza-5α-androst-1-ene-17β-carboxamide;

N-[1,1,1,3,3,3-hexafluoro-(4'-fluorophenyl)propyl]-3-oxo-4-aza-5α-androst-1-ene-17β-carboxamide;

N-[1,1,1,3,3,3-hexafluoro-(4'-chlorophenyl)propyl]-3-oxo-4-aza-5α-androst-1-ene-17β-carboxamide;

N-[1,1,1,3,3,3-hexafluoro-(4'-trifluoromethylphenyl)propyl]-3-oxo-4-aza-5α-androst-ene-17β-carboxamide;

N-[1,1,1,3,3,3-hexafluoro-(2',4'-dimethylphenyl)propyl]-3-oxo-4-aza-5α-androst-1-ene-17β-carboxamide;

N-[1,1,1,3,3,3 -hexafluoro-(4'-phenylphenyl)propyl]-3-oxo-4-aza-5α-androst-1-ene-17β-carboxamide; and N-[1,1,1,3,3,3-hexafluoro-(4'-cyanophenyl)propyl]-3-oxo-4-aza-5α-androst-1-ene-17β-carboxamide.

5. The method according to claim 1, wherein said compound of formula (I) is N-(1,1,1,3,3,3-hexafluorophenylpropyl)-3-oxo-4-aza-5α-androst-1-ene-17β-carboxamide.

* * * * *